United States Patent
Fast et al.

(10) Patent No.: US 10,258,035 B2
(45) Date of Patent: Apr. 16, 2019

(54) ETHER AMINES FOR ENHANCED SPORICIDAL PERFORMANCE

(71) Applicant: Ecolab USA Inc., St. Paul, MN (US)

(72) Inventors: Jonathan Fast, St. Paul, MN (US); Robert D. P. Hei, Baldwin, WI (US); Brandon L. Herdt, Hastings, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/440,495

(22) Filed: Feb. 23, 2017

(65) Prior Publication Data

US 2017/0245499 A1    Aug. 31, 2017

Related U.S. Application Data

(60) Provisional application No. 62/299,616, filed on Feb. 25, 2016.

(51) Int. Cl.

| | | |
|---|---|---|
| *A61L 2/18* | (2006.01) | |
| *A01N 37/16* | (2006.01) | |
| *C11D 3/48* | (2006.01) | |
| *A01N 33/16* | (2006.01) | |
| *B05B 11/00* | (2006.01) | |
| *C11D 7/26* | (2006.01) | |
| *C11D 7/32* | (2006.01) | |

(52) U.S. Cl.
CPC ............ *A01N 37/16* (2013.01); *A01N 33/16* (2013.01); *A61L 2/18* (2013.01); *B05B 11/3083* (2013.01); *C11D 3/48* (2013.01); *C11D 7/265* (2013.01); *C11D 7/3227* (2013.01); *A61L 2202/26* (2013.01); *B05B 11/3011* (2013.01)

(58) Field of Classification Search
CPC .......... A01N 37/16; A01N 33/08; A61L 2/18; A61L 2202/26; B05B 11/0078; C11D 3/48

See application file for complete search history.

(56) References Cited

U.S. PATENT DOCUMENTS

| | | |
|---|---|---|
| 5,863,874 A | 1/1999 | Person Hei |
| 6,214,777 B1 | 4/2001 | Li et al. |
| 7,723,281 B1 | 5/2010 | Herdt et al. |
| 8,685,112 B1 | 4/2014 | Smith et al. |
| 2002/0168422 A1 | 11/2002 | Hei et al. |
| 2006/0257498 A1 | 11/2006 | Stingl et al. |
| 2009/0143481 A1 | 6/2009 | Man et al. |
| 2009/0246336 A1 | 10/2009 | Burnett et al. |

OTHER PUBLICATIONS

International Search Report and Written Opinon for Application No. PCT/US2017/019146 dated Jun. 8, 2017.

*Primary Examiner* — Timothy C Cleveland
(74) *Attorney, Agent, or Firm* — Merchant & Gould P.C.

(57) ABSTRACT

A composition and method are used to treat articles suspected of contamination with bacterial spores. The composition and method are effective against bacterial spores selected from *C. diff.*, *C. botulinum*, *C. sporogenes*, *B. cereus*, and *B. subtilis*. The article can be a textile or a hard surface. The method includes preparing a first use solution by mixing ether amine in water and a second use solution by mixing percarboxylic acid in water; applying the first use solution to the article; and applying the second use solution to the article. An alternative method includes preparing a mixture of ether amine, percarboxylic acid, and water, and applying the mixture to the article.

32 Claims, 1 Drawing Sheet

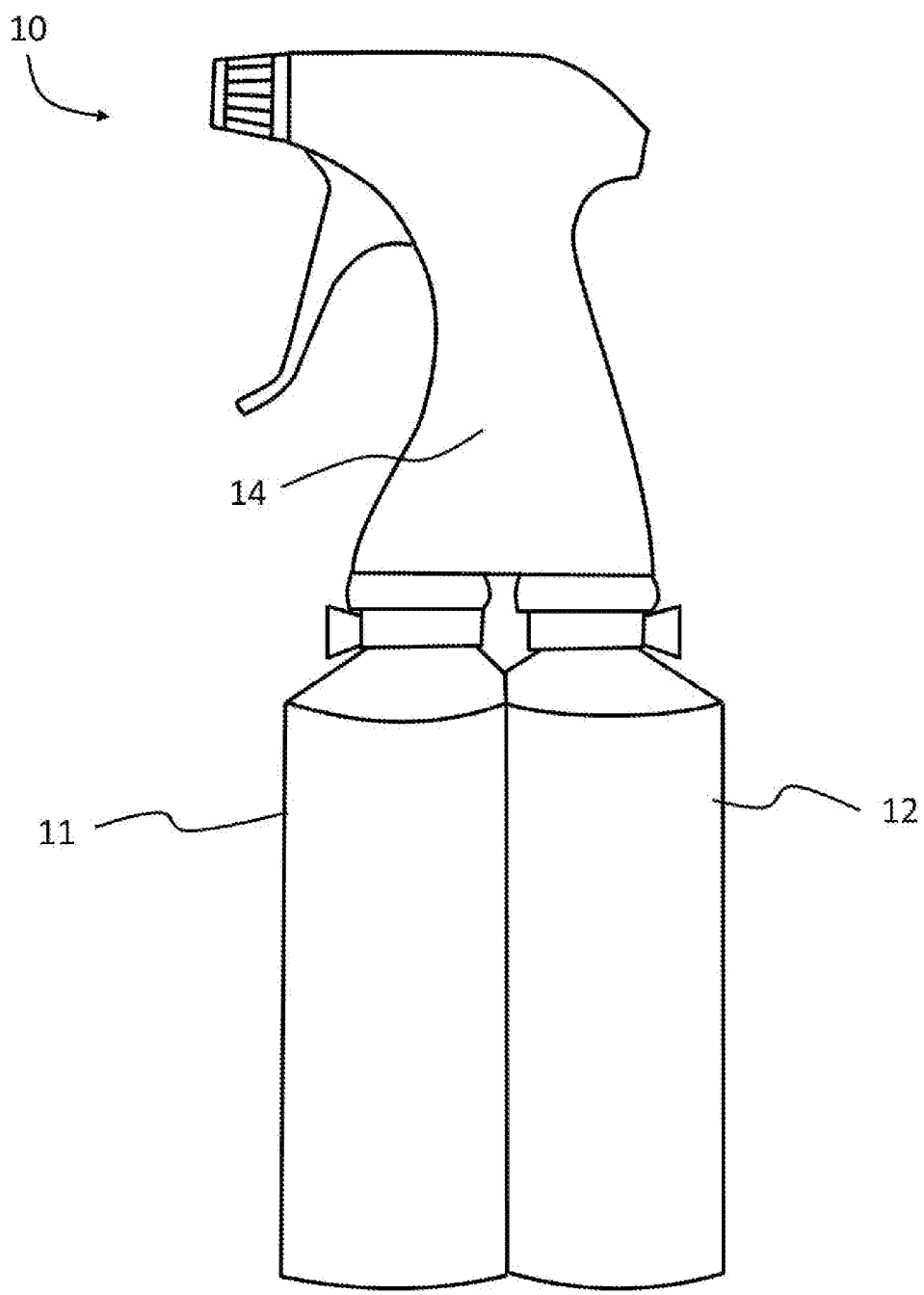

ETHER AMINES FOR ENHANCED SPORICIDAL PERFORMANCE

CROSS REFERENCE TO RELATED APPLICATIONS

This application claims the benefit of U.S. Provisional Application No. 62/299,616, filed on Feb. 25, 2016, which application is hereby incorporated by reference in its entirety.

FIELD

The present disclosure relates to a composition and method for providing a sporicidal effect. In particular, the present disclosure relates to compositions comprising one or more ether amines and their derivatives and one or more peracids, and methods for preparation and use of such compositions.

BACKGROUND

Control of bacteria and their spores is desirable in industrial and institutional settings, including industrial and institutional cleaning and laundry applications. For example, it is desirable to reduce or eliminate bacterial spores, such as spores of Clostridium difficile ("C. diff"), Clostridium botulinum ("C. botulinum"), Clostridium sporogenes ("C. sporogenes"), Bacillus cereus ("B. cereus"), and Bacillus subtilis ("B. subtilis") from surfaces, instruments, and from industrial and institutional laundry (e.g., health care facilities) to minimize the occurrence of diseases, such as gut infections cause by C. diff or B. cereus.

Standard oxidative chemistries, such as chlorine (e.g., hypochlorite) and peracids can be effective against C. diff spores, but typically require high concentrations of chemicals. Current CDC guidelines recommend hypochlorite concentrations between 1,000-5,000 ppm for disinfection of C. diff spores on hard surfaces. However, this concentration is at least an order of magnitude higher than the typical hypochlorite dose of 100 ppm for laundry sanitizing.

It would be beneficial to provide for a cost-effective, yet efficient, method for sanitizing and/or disinfecting laundry (soft surfaces) and hard surfaces. In particular, it would be beneficial to provide for an efficient and cost-effective composition and method for reducing or eliminating bacterial spores, including C. diff, in laundry and on hard surfaces. It would further be beneficial to provide for a composition having sporicidal activity and improved water solubility; to provide for a composition having sporicidal activity and improved stability in the presence of water hardness; and to provide for a method for eradicating spores by a composition with improved water solubility and stability.

SUMMARY

A composition and method are used to treat articles suspected of contamination with bacterial spores. The composition and method are effective against bacterial spores selected from C. diff., C. botulinum, C. sporogenes, B. cereus, and B. subtilis. The article can be a textile or a hard surface. The method includes preparing a first use solution by mixing ether amine in water and a second use solution by mixing percarboxylic acid in water; applying the first use solution to the article; and applying the second use solution to the article. An alternative method includes preparing a mixture of ether amine, percarboxylic acid, and water, and applying the mixture to the article.

BRIEF DESCRIPTION OF DRAWINGS

FIG. 1 is a two-chamber spray bottle used to house and apply the composition according to an embodiment.

DETAILED DESCRIPTION

The present disclosure relates to methods of treating laundry or various surfaces to reduce bacterial spores. The present disclosure further relates to compositions with sporicidal activity that exhibit improved solubility and stability in water.

As used in this invention, the term "sporicide" refers to a physical or chemical agent or process having the ability to cause greater than a 90% reduction (1-log order reduction) in the population of spores of Bacillus subtilis, Clostridium difficile, or Clostridium sporogenes within 30 min at room temperature.

According to some embodiments, the compositions and methods of the present disclosure are effective against spores of one or more of C. diff., C. botulinum, C. sporogenes, B. cereus, and B. subtilis. In at least one embodiment, compositions and methods are effective against spores of C. diff, C. botulinum, C. sporogenes, B. cereus, and B. subtilis. For example, embodiments of the present compositions have advantageous sporicidal activity against C. diff and other difficult-to-kill bacterial endospores, such as those of C. sporogenes and B. subtilis. Further, the present compositions are also active against vegetative bacteria, vegetative fungi, other bacterial spores, fungal spores, and viruses.

In certain embodiments, the sporicidal compositions provide greater than a 99% reduction (2-log order reduction), greater than a 99.9% reduction (3-log order reduction), greater than a 99.99% reduction (4-log order reduction), or greater than a 99.999% reduction (5-log order reduction) in populations of spores, or total inactivation of endospores within 30 min at room temperature. In an embodiment, the present sporicidal composition eliminates all bacterial endospores within the stated time and temperature, e.g., 30 min at room temperature. To test sporicidal efficiency, a test strip comprising bacterial spores can be used. Standard test methods for evaluating efficiency of the composition and method can be used, such as ASTM method E2274, as specified by the U.S. Environmental Protection Agency (EPA) Product Performance Test Guidelines, document OCSPP 810.2400. ASTM E2274 requires that the test strips be inoculated in a bacteria solution containing at least $10^8$ colony forming units (CFU) per mL. For the test to be valid, a minimum average of $1.0 \times 10^4$ CFU/carrier and $1.0 \times 10^4$ CFU/mL in the wash water should be recovered after the test from the control system.

The method and composition of the present disclosure can be used to treat a variety of surfaces, substances, and articles for which it is desirable to reduce microbial contamination, particularly microbial contamination arising from spores of microorganisms. Examples of such substances and articles include textiles (e.g., cottons, wools, silks, rayon, viscose, and synthetic fabrics such as polyesters, polyolefins, and acrylics, blends of fibers such as cotton-polyester blends, etc.), wood and cellulose-based systems (e.g., paper), food handling surfaces (e.g., countertops, food handling equipment and packaging, utensils), general premise surfaces (e.g., floors, walls, ceilings, exterior of furniture, etc.), or equipment surfaces (e.g., medical equipment, manufacturing equipment, processing equipment, etc.).

According to some embodiments, the compositions and methods of the present disclosure are more cost-effective than treatments using hypochlorite and/or peracids at concentrations that achieve the same level of efficiency.

According to at least some embodiments, the composition of the present disclosure comprises one or more ether amines, one or more peracids, and optionally other antimicrobial agents and detersive components, such as surfactants. The composition may also include additional components, such as solvents, salts, pH modifiers, fillers, coloring agents, fragrances, etc.

Use of dodecylamine has been found to be beneficial against spore germination of pathogenic bacteria, such as C. diff. However, inclusion of dodecylamine in an aqueous composition, such as a detergent composition, has been problematic because of the limited solubility of long chain amines particularly in the presence of water hardness. It has been discovered that ether amines in combination with peroxyacids show a synergistic sporicidal effect against bacterial spores, such as those of C. diff. It has further been discovered that ether amines exhibit good solubility and stability in water. A comparison of calculated solubilities for dodecylamine (CAS 124-22-1; a traditional amine) and 3-octyloxy-1-propanamine (CAS (15930-66-2; ether amine with the same chain length as dodecylamine) is shown in the table below.

TABLE 1

Solubility

| | Solubility g/L at 25° C. | |
|---|---|---|
| pH | Dodecylamine | 1-Propanamine, 3-(octyloxy)- |
| 6 | 150 | 1000 |
| 7 | 120 | 847 |
| 8 | 43 | 120 |
| 9 | 5.7 | 14 |
| 10 | 0.7 | 3.4 |

Calculated using Advanced Chemistry Development (ACD/Labs) Software V11.02

According to some embodiments, the composition is prepared from two parts, part I and part II, which can be applied consecutively, cumulatively, or simultaneously. When parts I and II are applied consecutively, an article can be treated first with part I and then with part II. When parts I and II are applied cumulatively, part I can first be applied to the article and then part II, without first removing part I. The parts may also be applied in reverse order, first applying part II and then part I, without first removing part II. In an embodiment, where the composition is used to treat laundry, the parts I and II can be applied directly to the wash solution to create the composition. Parts I and II can be applied to the wash solution consecutively, cumulatively or simultaneously. In another embodiment, where the composition is used to treat a surface (e.g., a hard surface), parts I and II can be applied directly to the surface (either consecutively, cumulatively or simultaneously), or can be first diluted and then applied to the surface, or can be mixed to produce a mixture of parts I and II that can then be applied to the surface.

The term "composition" is used here to refer to the use solution that may be a two-part solution with parts I and II, or a mixture comprising parts I and II. The designations "part I" and "part II" used here are arbitrary and should not be considered limiting.

Amines

In an embodiment, the present composition can include an effective amount (e.g., sporicidal amount) of ether amine. The ether amine can be provided as part I of the composition, or may be provided as part of a mixture of parts I and II.

Suitable ether amines include primary, secondary, or tertiary ether amines. Ether amines generally have the following formula: $N(R^a)(R^b)(R^c)$, where at least one of $R^a$, $R^b$, and $R^c$ includes an ether moiety. For example, the ether amine can be:

a primary ether amine of Formula 1: $R^1OR^2NH_2$;

a secondary ether amine of Formula 2: $(R^1OR^2)(R^3OR^4)NH$ or Formula 3: $(R^1OR^2)R^3NH$;

a tertiary ether amine of Formula 4: $(R^1OR^2)(R^3OR^4)N(R^5OR^6)$, Formula 5: $(R^1OR^2)(R^3OR^4)NR^5$, or Formula 6: $(R^1OR^2)R^3NR^5$;

a diamine of Formula 7: $R^1OR^2NHR^3NH_2$; or a mixture thereof.

In suitable ether amines, $R_1$, $R_2$, $R_3$, $R_4$, $R_5$, and $R_6$ may be independently selected from C1-C22 alkyl groups. In preferred embodiments, $R_1$ comprises a relatively longer carbon chain, whereas $R_2$-$R_6$ comprise shorter carbon chains. The alkyl groups may be saturated or unsaturated, aliphatic or cyclic, unsubstituted or substituted, linear or branched. The ether amine may be in salt form, such as an ether ammonium salt. In an embodiment, the composition comprises one or more diamines.

Examples of suitable ether amines include alkyloxyalkylamines, such as hexyloxypropylamine, tetradecyloxypropyl-1,3-propylamine, and dodecyloxypropyl-1,3-propylamine; branched alkyloxyalkylamines, such as ethylhexyloxypropylamine, isotridecyloxypropylamine, and isodecyloxypropylamine; or alkyloxydiamines, such as octyloxypropyl-1,3-propylenediamine, decyloxypropyl-1,3-propylenediamine, isodecyloxypropyl-1,3-propylenediamine, dodecyloxypropyl-1,3-propylenediamine, tetradecyloxypropyl-1,3-propylenediamine, or isotridecyloxypropyl-1,3-propylenediamine.

Ether amines are commercially available, for example, from Air Products and Chemicals, Inc. in Allentown, Pa.; Clariant Corp. in Charlotte, N.C.; and BASF Corporation in Florham Park, N.J. Available products include, for example, Air Products' TOMAMINE® PA-19, PA-1618, PA-1816, DA-18, DA-19, DA-1618, and DA-1816. In an embodiment, the composition comprises PA-14, DA-1214, DA-1618, or a combination thereof.

Peracids

According to at least one embodiment, the composition comprises one or more peroxycarboxylic acids (also known as peracids) or salts thereof, or hydrogen peroxide. In some embodiments, the composition comprises an aqueous equilibrium of carboxylic acid and corresponding peroxycarboxylic acid. Such an equilibrium also typically includes an equilibrium amount of hydrogen peroxide. For example, the composition may comprise acetic acid, peroxyacetic acid, and hydrogen peroxide in equilibrium. The peroxycarboxylic acid can also be provided as a precursor (e.g., an ester precursor) that can be converted to peroxycarboxylic acid (e.g., by reacting the ester precursor with hydrogen peroxide). The peroxycarboxylic acid or hydrogen peroxide can be provided as part II of the composition, or may be provided as part of a mixture of parts I and II.

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three. The R-group can be saturated or unsaturated as well as substituted or unsubstituted. Peroxycarboxylic acids are typically named by prefixing the parent acid with peroxy.

The composition and methods of the invention can employ short and/or medium chain peroxycarboxylic acids containing, for example, from 2 to 11, from 2 to 7, or from 2 to 5 carbon atoms. For example, medium chain peroxycarboxylic (or percarboxylic) acids can have the formula $R(CO_3H)_n$, where R is a $C_1$-$C_6$ alkyl group, a $C_3$-$C_{11}$ cycloalkyl, a $C_5$-$C_{11}$ arylalkyl group, $C_5$-$C_{11}$ (e.g., $C_6$) aryl group, or a $C_5$-$C_{11}$ heterocyclic group; and n is one, two, or three. Peroxyacetic (or peracetic) acid is a peroxycarboxylic acid having the formula $CH_2COOOH$. Peroxyhexanoic (or perhexanoic) acid is a peroxycarboxylic acid having the formula, for example, of n-peroxyhexanoic acid: $CH_3(CH_2)_4COOOH$. The carbon chain of the peroxycarboxylic acid can be a straight chain alkyl moiety, an acid with a branched alkyl moiety, or a mixture thereof.

Suitable peroxycarboxylic acids include short chain peroxycarboxylic acids and medium chain peroxycarboxylic acids and mixtures therefor. For example, suitable peroxycarboxylic acids include peroxyacetic, peroxybutanoic, peroxypropanoic, peroxypentanoic, peroxyhexanoic, peroxyheptanoic, peroxyoctanoic, peroxysalicylic, and peroxybenzoic acids. In certain embodiments, the peroxycarboxylic acid comprises peroxyacetic acid, peroxybutanoic acid, peroxypropanoic acid, peroxypentanoic acid, peroxyhexanoic acid, peroxyoctanoic, or a mixture thereof. In an embodiment, the peroxycarboxylic acid includes or is peroxyacetic acid.

In some embodiments it may be desirable to choose the peroxycarboxylic acid with a short chain length that is not hydrophobic. For example, the peroxycarboxylic acid may have a chain length of 4 carbons or less. Particularly if the peroxycarboxylic acid is added to a solution together with the ether amine, hydrophobicity caused by a longer chain length may cause the peroxycarboxylic acid and ether amine to agglomerate, thus reducing the efficacy of the solution.

According to some embodiments, the composition comprises one or more carboxylic acids. Carboxylic acids can have one, two, three, or more carboxyl groups. The composition and methods of the invention typically employ short and/or medium chain carboxylic acids containing, for example, from 2 to 12, from 2 to 9, or from 2 to 5 carbon atoms. For example, medium chain carboxylic acids can have the formula R—COOH in which R can be a $C_1$-$C_{11}$ alkyl group, a $C_3$-$C_{11}$ cycloalkyl group, a $C_5$-$C_{11}$ arylalkyl group, $C_5$-$C_{11}$ (e.g., $C_6$) aryl group, or a $C_5$-$C_{11}$ heterocyclic group. Suitable carboxylic acids include acetic acid, butanoic acid, propanoic acid, pentanoic acid, hexanoic acid, heptanoic acid, octanoic acid, salicylic acid, benzoic acid, mixtures thereof, or the like. The alkyl backbones of the medium chain carboxylic acids can be straight chain, branched, or a mixture thereof.

According to embodiments, the composition comprises an effective amount of ether amines and peroxygen compounds (e.g., peracids), applied either separately as parts I and II, or as a mixture of parts I and II. The composition may comprise about 10 to 2,000 ppm, about 20 to 1,500 ppm, about 25 to 1,000 ppm, about 30 to 800 ppm, about 40 to 600 ppm, about 50 to 500 pm, or about 100 to 5,000 ppm of ether amines. For example, the composition may comprise about 10 ppm, about 20 ppm, about 30 ppm, about 40 ppm, about 50 ppm, about 75 ppm, about 100 ppm, about 125 ppm, about 150 ppm, about 200 ppm, about 250 ppm, about 300 ppm, about 400 ppm, about 500 ppm, about 750 ppm, about 1,000 ppm, about 1,250 ppm, or about 1,500 ppm ether amines, or any amount therebetween. If the ether amine comprises two or more different ether amines, the ether amines may be present at any ratio relative to one another. In an exemplary embodiment, the ether amines are provided in part I of the composition.

The composition may comprise about 10 to 10,000 ppm, or about 20 to 8,000 ppm, or about 50 to 6,000 ppm, about 50 to 3,000 ppm, about 50 to 1,500 ppm, about 50 to 1,000 ppm, about 20 to 500 pm, or about 50 to 5,000 ppm of peracids. For example, the composition may comprise about 10 ppm, about 20 ppm, about 30 ppm, about 40 ppm, about 50 ppm, about 75 ppm, about 100 ppm, about 125 ppm, about 150 ppm, about 200 ppm, about 250 ppm, about 300 ppm, about 400 ppm, about 500 ppm, about 750 ppm, about 1,000 ppm, about 1,250 ppm, about 1,500 ppm, about 2,000 ppm, about 2,500 ppm, about 3,000 ppm, about 4,000 ppm, about 5,000 ppm, about 7,500 ppm, or about 10,000 ppm peracids, or any amount therebetween. If the peracid comprises two or more different peracids, the peracids may be present at any ratio relative to one another.

Exemplary embodiments of the composition are shown in TABLE 2 below. The ether amines and peracids may be provided in separate parts of the composition, e.g., part I and part II, respectively, or as a mixture of parts I and II.

TABLE 2

Ether amine and peracid concentrations.

| | Ether Amines (ppm) | Peracids (ppm) |
| --- | --- | --- |
| Composition A | 15-200 | 50-500 |
| Composition B | 15-200 | 500-1000 |
| Composition C | 50-300 | 100-500 |
| Composition D | 50-300 | 500-1200 |
| Composition E | 250-500 | 100-500 |
| Composition F | 250-500 | 500-1500 |
| Composition G | 500-1000 | 500-1000 |
| Composition H | 500-1000 | 1000-2000 |

In a preferred embodiment, the composition comprises about 2500 ppm or less of ether amines and about 1000 ppm or less of peracids. In another preferred embodiment, the composition comprises about 50 to 1000 ppm of ether amines, and about 200 to 750 ppm of peracids.

In an embodiment, the composition comprises a two-part composition with part I and part II. Parts I and II can be provided as concentrates that may be diluted with a solvent prior to use. For example, parts I and II may be concentrated solutions of ether amines and peracids (respectively) that are added to a use solution (e.g., a wash solution to wash laundry, or to a spray to be applied to textiles or surfaces) in a suitable amount to create a sporicidal effect. The composition (or its parts) may be provided as a concentrate that may be diluted about 1:1, about 1:5, about 1:10, about 1:100, about 1:100-1:1,000, about 1:500-1:2,000, about 1:1,000-1:10,000, about 1:5,000-1:100,000, or about 1:1,000-1:100,000 to prepare a use solution. The part I concentrate solution may comprise ether amines at about 95 to 100 wt-% (when ether amine is provided "neat," without significant dilution), or at about 1 to about 25 wt-%, about 5 to about 20 wt-%, or about 5 to about 10 wt-%. The part II concentrate solution may comprise peracids at about 1 to about 35 wt-%, about 2 to about 25 wt-%, about 4 to about 20 wt-%, or about 5 to about 15 wt-%. Alternatively the peracid may be prepared by mixing the corresponding carboxylic acid with hydrogen peroxide and allowing the mixture to equilibrate, or may be prepared from a precursor, such as a suitable ester. The ether amines may comprise one or more different ether amines. Similarly, the peracids may comprise one or more different peracids. Suitable solvents for diluting the concentrate include water and aqueous solvents, such as aqueous alcohols or other suitable solvents.

In some embodiments, the composition is a mixture of ether amine, peracid, and water, and optionally one or more additional components. For example, the mixture may contain from about 10 to about 1,500 ppm, from about 20 to about 1,000 ppm, from about 50 to about 500 ppm, or from about 75 to about 300 ppm ether amines; and from about 10 to about 1,500 ppm, from about 20 to about 1,000 ppm, from about 50 to about 500 ppm, or from about 75 to about 300 ppm peracids.

Additional Components

In some embodiments, the composition can be provided as a booster (e.g., a laundry booster), added to a use or wash solution in addition to another composition, such as laundry detergent. In other embodiments, the composition is formulated as a complete detergent composition, including for example, suitable surfactants and other components. In yet other embodiments, the composition can comprise two or more parts of a multi-part system, where different parts can be applied or used simultaneously or consecutively. Such multi-part system can comprise a complete detergent composition or be formulated to be mixed with other components to provide a use or wash solution.

The composition may include any number of additional agents or adjuvants. Specifically, the composition may comprise one more of an antimicrobial agent, surfactant, defoaming agent, wetting agent, potentiator (also referred to as a synergist to the active ingredients), thickener, stabilizing agent, hydrotrope or coupling agent, aesthetic enhancing agent (e.g., a colorant, odorant, fragrance, or masking agent), manufacturing processing aid, preserving agent, or tracer. Such adjuvants can be formulated with the sporicidal composition or added to the system simultaneously, or after, the addition of the sporicidal composition. In some embodiments the composition is formulated for use with laundering, and the composition can be formulated to comprise non-irritating components. In some other embodiments the composition is formulated for use with food contact surfaces, and the composition may include food grade components.

The composition may optionally comprise additional antimicrobial agents. Additional antimicrobial agent can be added to use compositions before use. Examples of suitable antimicrobial agents include active oxygen compounds, halogen containing compounds, amine or quaternary ammonium compounds, sulfonic acids, phenolic derivatives, or the like. Common active oxygen compounds include, for example, hydrogen peroxide, percarbonate, perborate, and the like. Halogen containing antibacterial agents include sodium trichloroisocyanurate, sodium dichloro isocyanate (anhydrous or dihydrate), iodine-poly(vinylpyrolidinone) complexes, bromine compounds such as 2-bromo-2-nitropropane-1,3-diol, and quaternary antimicrobial agents such as benzalkonium chloride, didecyldimethyl ammonium chloride, choline diiodochloride, tetramethyl phosphonium tribromide. Amine or quaternary ammonium compounds include, for example, alkyl dimethylbenzyl ammonium chloride, dialkyldimethyl ammonium chloride, and N-dialkylethylbenzyl ammonium chloride. A suitable sulfonic acid can be, for example, dodecylbenzene sulfonic acid. Phenolic antimicrobials include pentachlorophenol, ortho-phenylphenol, a chloro-p-benzylphenol, p-chloro-m-xylenol tert-amyl phenol, and $C_1$-$C_6$ alkyl hydroxy benzoates. Other antimicrobial compositions include hexahydro-1,3,5-tris(2-hydroxyethyl)-s-triazine, dithiocarbamates such as sodium dimethyldithiocarbamate, and a variety of other materials are known in the art for their antimicrobial properties.

In some embodiments, an antimicrobial component can be included in the range of 0.001 to 25 wt-% of the composition, about 0.01 to 15 wt-%, or about 0.05 to about 10 wt-%.

The composition may comprise one or more surfactants. Suitable surfactants include water-soluble or water-dispersible nonionic, anionic, cationic, amphoteric, semi-polar nonionic surfactants, and zwitterionic surface active agents. In some embodiments, the composition comprises low-foaming or non-foaming surfactants.

The one or more surfactants can be added in the composition at any suitable concentration. As with any charged components, care should be taken not to cause any inadvertent negative effects, such as issues with solubility. The surfactants can be present in a use solution at a concentration range of about 100 to 7000 ppm, about 250 to 6500 ppm, about 400 to 6000 ppm, about 600 to 5500 ppm, or about 1000 to 5000 ppm. The amount of surfactants in the composition can be adjusted according to the intended dilution (if any) and end use. For example, in typical laundry applications the amount of surfactant in the use solution is more diluted and may be about 200-1200 ppm, whereas in a typical hard surface cleaning application the amount of surfactant in the use solution may be about 1500-5000 ppm.

Nonionic Surfactants

Examples of suitable nonionic surfactants include alkoxylated surfactants. Suitable alkoxylated surfactants include alcohol ethoxylates, EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like. When employed as a solvent a surfactant, such as a nonionic surfactant, can be at concentrations higher than those conventionally employed as surfactant.

Cationic Surfactants

Surface active substances are classified as cationic if the charge on the hydrotrope portion of the molecule is positive. In theory, cationic surfactants may be synthesized from any combination of elements containing an "onium" structure $R_nX^+Y^-$— and could include compounds other than nitrogen (ammonium) such as phosphorus (phosphonium) and sulfur (sulfonium). In practice, the cationic surfactant field is dominated by nitrogen containing compounds. Cationic surfactants preferably include compounds containing at least one long carbon chain hydrophobic group and at least one positively charged ion.

Examples of suitable cationic surfactants include quaternary ammonium salts, e.g., alkylquaternary ammonium chloride surfactants such as alkyldimethylbenzylammonium chloride (ADBAC) or dialklyldimethylammonium chloride (DADMAC), and n-tetradecyldimethylbenzylammonium chloride monohydrate, and a naphthylene-substituted quaternary ammonium chloride such as dimethyl-1-naphthylmethylammonium chloride; amines such as primary, secondary and tertiary monoamines with alkyl or alkenyl chains, ethoxylated alkylamines, alkoxylates of ethylenediamine, imidazoles such as a 1-(2-hydroxyethyl)-2-imidazoline, a 2-alkyl-1-(2-hydroxyethyl)-2-imidazoline, and the like.

Anionic Surfactants

Suitable anionic surfactants include sulfonic acids and their salts (sulfonates), phosphate esters, carboxylates, mixtures thereof, and the like. Persons skilled in the art will recognize the need to avoid causing unintentional reactions between anionic surfactants and other charged surfactants, such as ether amines, and would recognize that the amount of anionic surfactants needs to be balanced with the amounts of such other charged surfactants. Preferably, the concentration of anionic surfactants in the use solution is in the range of 0 ppm to 600 ppm, or about 10 ppm to 500 ppm, or about 20 ppm to 200 ppm. For example, the use solution may comprise up to 500 ppm, 400 ppm, 300 ppm, 250 ppm, or 200 ppm anionic surfactants.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like.

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Semi-Polar Nonionic Surfactants

The composition may further comprise one or more semi-polar nonionic surfactants. Suitable semi-polar nonionic surfactants include, for example, phosphine oxides, sulfoxides and their alkoxylated derivatives.

Amphoteric Surfactants

Amphoteric, or ampholytic, surfactants contain both a basic and an acidic hydrophilic group and an organic hydrophobic group. These ionic entities may be similar to the anionic or cationic groups comprised in the other types of surfactants. Typical functional groups in amphoteric surfactants include a basic nitrogen group and an acidic carboxylate group. In some amphoteric surfactants the negative charge is provided by a sulfonate, sulfate, phosphonate, or phosphate group.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

The composition may comprise one or more defoaming agents. Suitable defoaming agents include, for example, silicones, aliphatic acids or esters; alcohols; sulfates or sulfonates; amines or amides; vegetable oils, waxes; mineral oils as well as their sulfated derivatives; fatty acid soaps such as alkali, alkaline earth metal soaps; and mixtures thereof. Examples of suitable silicone defoaming agents include dimethyl silicone, glycol polysiloxane, methylphenol polysiloxane, trialkyl or tetraalkyl silanes, and hydrophobic silica defoamers. The defoaming agents can be present at a concentration range of about 0.01 wt-% to 5 wt-%, about 0.01 wt-% to 2 wt-%, or about 0.01 wt-% to about 1 wt-%.

The composition may comprise one or more wetting agents. Wetting agents function to increase the surface contact or penetration activity of the sporicidal composition.

The composition may comprise one or more thickeners or gelling agents. Suitable thickeners include, for example, inorganic thickeners, organic thickeners, oligomeric thickeners, and associative thickeners. These may include natural gums such as xanthan gum, guar gum, or other gums from plant mucilage; modified cellulose derivatives; oligomeric organic thickeners; and hydrocolloid thickeners, such as pectin; and inorganic silicates and clays. In an embodiment, the thickener does not leave contaminating residue on the surface of an object. The thickeners or gelling agents can be compatible with food or other sensitive products in contact areas. Generally, the concentration of thickener employed in the present compositions will be dictated by the desired viscosity of the final composition or use solution. However, as a general guideline, the quantity of thickener suitable for use in the present composition ranges from about 0.1 wt-% to about 1.5 wt-%, about 0.1 wt-% to about 1 wt %, or about 0.1 wt-% to about 0.5 wt-%.

The composition can optionally be formulated as a solid (e.g., a cast or pressed block, a powder, or a granulated powder) by using a solidification agent. In an exemplary embodiment, the composition is formulated in block form with a detergent. Examples of suitable solidification agents include solid polyethylene glycol (PEG), solid polypropylene glycol, solid EO/PO block copolymer, amide, urea (also known as carbamide), nonionic surfactant (which can be employed with a coupler), starch that has been made water-soluble (e.g., through an acid or alkaline treatment process), cellulose that has been made water-soluble, inorganic agent, poly(maleic anhydride/methyl vinyl ether), polymethacrylic acid, other generally functional or inert materials with high melting points, mixtures thereof, and the like.

Exemplary glycol solidification agents include a solid polyethylene glycol or a solid polypropylene glycol, which can, for example, have molecular weight of about 1,400 to about 30,000. In certain embodiments, the solidification agent includes or is solid PEG, for example PEG 1500 up to PEG 20,000. In certain embodiments, the PEG includes PEG 1450, PEG 3350, PEG 4500, PEG 8000, PEG 20,000, and the like. Suitable solid polyethylene glycols are commercially available from Union Carbide under the tradename CARBOWAX.

Exemplary amide solidification agents include stearic monoethanolamide, lauric diethanolamide, stearic diethanolamide, stearic monoethanol amide, cocodiethylene amide, an alkylamide, mixtures thereof, and the like.

Exemplary nonionic surfactant solidification agents include nonylphenol ethoxylate, linear alkyl alcohol ethoxylate, ethylene oxide/propylene oxide block copolymer, mixtures thereof, or the like. Exemplary ethylene oxide/propylene oxide block copolymers include those sold under the Pluronic tradename (e.g., Pluronic 108 and Pluronic F68) and commercially available from BASF Corporation. In some embodiments, the nonionic surfactant can be selected to be solid at room temperature or the temperature at which the composition will be stored or used. In other embodiments, the nonionic surfactant can be selected to have reduced aqueous solubility in combination with the coupling agent. Suitable couplers that can be employed with the nonionic surfactant solidification agent include propylene glycol, polyethylene glycol, mixtures thereof, or the like.

Exemplary inorganic solidification agents include phosphate salt (e.g., alkali metal phosphate), sulfate salt (e.g., magnesium sulfate, sodium sulfate or sodium bisulfate), acetate salt (e.g., anhydrous sodium acetate), borates (e.g., sodium borate), silicates (e.g., the precipitated or fumed forms (e.g., Sipernat 50® available from Degussa), carbonate salt (e.g., calcium carbonate or carbonate hydrate), other known hydratable compounds, mixtures thereof, and the like. In an embodiment, the inorganic solidification agent includes organic phosphonate compound and carbonate salt, such as an E-Form composition.

In some embodiments, the compositions include any agent or combination of agents that provide a requisite degree of solidification and aqueous solubility. In other embodiments, increasing the concentration of the solidification agent in the present composition can tend to increase the hardness of the composition. In yet other embodiments, decreasing the concentration of solidification agent can tend to loosen or soften the concentrate composition.

The composition may comprise one or more stabilizing agents, for example, to stabilize peracid and hydrogen peroxide in the composition and to prevent premature degradation of the constituents.

Suitable stabilizing agents include chelating agents or sequestrants. Suitable agents include organic chelating compounds that sequester metal ions in solution, particularly transition metal ions. For example, suitable agents include organic amino- or hydroxy-polyphosphonic acid complexing agents (either in acid or soluble salt forms), carboxylic acids (e.g., polymeric polycarboxylate), hydroxycarboxylic acids, or aminocarboxylic acids.

The sequestrant can be or can include phosphonic acid or phosphonate salt. Suitable phosphonic acids and phosphonate salts include 1-hydroxy ethylidene-1,1-diphosphonic acid (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono-, di-, or tetra-ethanolamine salts; or mixtures thereof.

Commercially available chelating agents include phosphonates sold under the trade name DEQUEST® (available from Monsanto Industrial Chemicals Co., St. Louis, Mo.) including, for example, 1-hydroxyethylidene-1,1-diphosphonic acid (DEQUEST® 2010); amino(tri(methylenephosphonic acid)) (DEQUEST® 2000); ethylenediamine[tetra (methylenephosphonic acid)] (DEQUEST® 2041); and 2-phosphonobutane-1,2,4-tricarboxylic acid (e.g., BAYHIBIT® AM available from Lanxess GmbH in Leverkusen, Germany).

In some embodiments, the present composition includes stabilizing agent at about 001 to 3 (e.g., 2.5) wt-%, about 0.01 to 2 (e.g., 2.5) wt-%, or about 0.01 to 1.5 wt-%.

The composition may comprise one or more hydrotropes, also referred to as coupling agents. A hydrotrope can increase the miscibility, solubility or phase stability of organic and inorganic materials in aqueous solution, and can be useful in a composition containing a carboxylic acid or peroxycarboxylic acid, A hydrotrope can also facilitate long term physical stability and/or homogeneity of a composition.

Examples of suitable hydrotropes include nonaqueous liquid carriers or solvents. Suitable solvents include propylene oxide glycol ether (e.g., DOWANOL® P Series, available from Dow Chemical, Midland, Mich.) or an ethylene oxide based glycol ether. Suitable propylene oxide glycols include a dipropylene glycol n-propyl ether sold under the tradename DOWANOL by Dow Chemical.

A stabilizing hydrotrope or coupling agent can be present in the composition at, for example, about 0.01 to 5 wt-%, about 0.05 to 4 wt-%, or about 0.05 to 3 wt-%.

The pH of the composition may be adjusted to provide optimal sporicidal, antimicrobial, and/or detersive activity. The pH may further be adjusted for the intended use, such as use with laundry or for cleaning surfaces or objects.

For example, in an embodiment where the composition is used in a laundry application and where the amine is added to the laundry first (e.g., as part I of the composition), the pH of the wash solution may be adjusted to a pH of about 7-12, or to about 9-11. The pH of the solution may be optimized based on various factors, such as water hardness and other components included in the composition (e.g., part I of the composition), or included in a laundry detergent that may be present in the wash solution at the time the composition is added. If the peracid is added to the wash solution, the pH of the wash solution is lowered and may become neutral or acidic. For example, when the peracid is added, the pH of the wash solution may be from about 3 to about 9, from about 4 to about 8, or from about 4 to about 6, depending on what the pH of the wash solution was prior to adding the peracid. If the pH of the wash solution was elevated prior to adding the peracid, e.g., to about 10 to about 11, the addition of the peracid composition (e.g., part II of the composition) may lower the pH to about 7 to 8.

In an embodiment where the composition is used to clean surfaces, such as hard surfaces, semi-hard surfaces (e.g., wood or textile-covered surfaces), or medical or dental instruments, the pH of the composition may be from about 3 to about 10.5, from about 3.5 to about 10, or from about 4 to about 9.

Suitable pH modifiers include bases and acids. Examples of bases include alkali metal hydroxides (e.g., sodium hydroxide or potassium hydroxide), amines, carbonates, bicarbonates, and silicates. Examples of acids include organic acids, such as carboxylic acids, and inorganic acids.

The composition can optionally include a buffer. Examples of suitable buffers include phosphates, carbonates, bicarbonates, and citrates. Exemplary phosphates include anhydrous mono-, di-, or trisodium phosphate, sodium tripolyphosphate, tetrasodium pyrophosphate and tetrapotassium pyrophosphate. Exemplary carbonates include sodium carbonate, potassium carbonate, and sesquicarbonate. Exemplary citrates include sodium or potassium citrate.

The composition may optionally include one or more additional functional ingredients including but not limited to dyes or pigments, or perfumes.

Dyes, Pigments, and Perfumes.

Various dyes, pigments, perfumes, and other aesthetic enhancing agents may optionally be included in the composition. Dyes may be included to alter the appearance of the composition, as for example, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like. Fragrances or perfumes that may be included in the compositions include, for example, terpenoids such as citronellol, aldehydes such as amyl cinnamaldehyde, a jasmine such as C1S-jasmine or jasmal, SZ-6929 (commercially available from Sozio Fragrance), vanillin, and the like.

In one embodiment, the composition is provided in a spray bottle and applied by spraying. For example, the composition may be provided in a two-chamber spray bottle 1 shown in FIG. 1, where part I is in the first chamber 11 and part II is in the second chamber 12. Parts I and II get mixed upon application when the composition is sprayed from the spray bottle 1. The spray bottle 1 may include an adjustable mixing assembly 14 that allows for the parts to be mixed at a desired ratio. In one exemplary embodiment, the composition is provided as a kit comprising a spray bottle having two chambers and an adjustable spray assembly in fluid communication with both chambers, where part I is housed in one of the two chambers and comprises about 10 to about 2,000 ppm of ether amine in water; and part II is housed in another of the two chambers and comprises about 10 to about 2,000 ppm of percarboxylic acid in water.

Methods of Using the Compositions

The disclosed compositions are particularly suitable for use in laundering textiles and cleaning surfaces, such as hard surfaces, semi-hard surfaces (e.g., wood or textile-covered surfaces), furniture, equipment, and instruments, such as medical and dental instruments. Medical instruments may include, for example, surgical instruments and endoscopic instruments. The composition can be formulated with the desired end-use in mind.

The composition can be used at room temperature or at higher or lower temperatures, such as at about 10° C. to about 99° C., about 15° C. to about 90° C., about 20° C. to about 80° C., about 25° C. to about 70° F. In some examples the composition is used at room temperature, e.g., at about 18° C. to about 30° C., or at about 18° C. to about 26° C. In some other examples, the composition is used at an elevated temperature, such as about 40° C., about 50° C., or about 60° C. The effectiveness of the composition may be increased at elevated temperatures.

In laundry applications, the composition can be applied to the wash water directly, either by dosing the components separately (simultaneously or consecutively), or by dosing a mixture of components. The composition can be dosed as a concentrate or as a diluted use-solution. The composition may be dosed into the wash solution before or after applying the wash solution onto the textiles, or can be applied directly onto the textiles. The composition may be used as a pretreatment or as a post-treatment (e.g., as a rinse). The composition can also be formulated as a detergent composition or be used simultaneously with a detergent composition.

According to embodiments, the dosage sequence of the ether amine component and the peracid component can be varied, in part, based on the concentration of the components. The term "dosage" is used here to refer to the final concentration of the components in the use solution (e.g., the wash solution). In some embodiments, when the dosage of the ether amine is about 2,000 ppm or less (e.g., between about 10 ppm and 2,000 ppm), and the dosage of the peracid is about 2,000 ppm or less (e.g., between about 10 ppm and 2,000 ppm), the components can be dosed simultaneously. In certain other embodiments, when the dosage of the ether amine is more than about 2,000 ppm (e.g., between about 2,000-10,000 ppm), the components are dosed sequentially. For example, in some embodiments, the ether amine component is dosed into a first wash solution first and the first wash solution is applied to the textiles; the first wash solution is drained, and the peracid composition is applied to a second wash solution that is applied to the textiles. After the second wash solution is drained, the textiles can be rinsed or subjected to another wash cycle (optionally with a detergent composition). It will be appreciated by those skilled in the art that embodiments of the methods disclosed here also encompass more complicated dosing sequences. For example, more sequential steps can be added to the method, dosing each of the components more than once, optionally at different concentrations, varying the order of dosing.

According to some embodiments, the composition can be used to treat surfaces, such as food handling surfaces (e.g., countertops, food handling equipment and utensils), general premise surfaces (e.g., floors, walls, ceilings, exterior of furniture, etc.), or equipment surfaces (e.g., medical equipment, manufacturing equipment, processing equipment, etc.). The composition can be applied to the surface to be treated by any suitable method, such as spraying, pouring, dripping, wiping, or mopping, etc. The composition can be provided as, for example, a ready-to-use spray or cleaning wipe. In one embodiment, the composition is applied to the surface as a mixture comprising ether amine and peracid. In another embodiment, the composition is a two part composition, where part I is applied to the surface first, and part II second. A two-part composition can also be used by mixing parts I and II together prior to application to a surface or to an object.

EXAMPLES

Various compositions were prepared and tested for removal of microbial spores from cotton fabric and from a glass surface. The experimental conditions and results are detailed in the Examples below.

Example 1

Aqueous solutions of ether amine (Part I) and peracid (Part II) were prepared. Ether amine (octyl/decyloxypropyl-1,3-diaminopropane) solution (Part I) was prepared in deionized water and the pH was adjust to 9.0 using glycolic acid. TOMAMINE DA1214 was used as the ether amine. TOMAMINE DA1214 contains about 50-60% by weight of 1,3-Propanediamine, N-[3-(octylocy)propyl] and about 35-40% by weight of 1,3-Propanediamine, N-[3-(decylocy)propyl], and is available from Air Products and Chemicals, Inc., in Allentown, Pa. Peracid (peracetic acid) solution (Part II) was prepared from TSUNAMI® 100 (15 peracetic acid), available from Ecolab Inc., in St Paul, Minn.

Cotton fabric swatches (5 mm×5 mm) were inoculated with *C. Diff.* AATCC 43598 at 35° C. for 48 hours. After inoculation, the swatches were treated with a first solution comprising part I of the composition at 50° C. for a first exposure time; removed from the first solution with sterile forceps and immediately transferred into a second solution comprising part II of the composition for a second exposure time. In comparative treatments, the solutions included only water. After treatment, the number of surviving spores was evaluated, and the log reduction of spores was compared to the comparative treatment (water only).

In Example 1, the first exposure time was 10 minutes (Part I) and the second exposure time was 5 minutes (Part II).

Three experiments were conducted. The results are shown in TABLES 3A-3C below.

TABLE 3A

Fabric Swatches, Consecutive Treatment

| Part I ether amine (ppm) | Part II peracid (ppm) | Average Survivors | Average Log | Log Reduction |
|---|---|---|---|---|
| 0 | 0 | $2.4 \times 10^6$ | 6.38 | — |
| 5000 | 300 | $1.4 \times 10^4$ | 4.15 | 2.23 |
| 0 | 300 | $2.3 \times 10^5$ | 5.36 | 1.02 |
| 5000 | 500 | <10 | <1.0 | 5.38 |
| 0 | 500 | $1.7 \times 10^3$ | 3.23 | 3.15 |
| 5000 | 0 | $1.3 \times 10^6$ | 6.11 | 0.27 |

TABLE 3B

Fabric Swatches, Consecutive Treatment

| Part I ether amine (ppm) | Part II peracid (ppm) | Average Survivors | Average Log | Log Reduction |
|---|---|---|---|---|
| 0 | 0 | $1.3 \times 10^6$ | 6.11 | — |
| 5000 | 300 | $3.1 \times 10^4$ | 4.49 | 1.62 |
| 2000 | 300 | $3.0 \times 10^1$ | 1.48 | 4.63 |
| 500 | 300 | $5.5 \times 10^1$ | 1.74 | 4.37 |
| 100 | 300 | $4.0 \times 10^1$ | 1.60 | 4.51 |

TABLE 3C

Fabric Swatches, Consecutive Treatment

| Part I ether amine (ppm) | Part II peracid (ppm) | Average Survivors | Average Log | Log Reduction |
|---|---|---|---|---|
| 0 | 0 | $5.4 \times 10^5$ | 5.73 | — |
| 100 | 300 | $2.0 \times 10^1$ | 1.30 | 4.43 |
| 75 | 300 | $2.5 \times 10^1$ | 1.40 | 4.33 |
| 50 | 300 | $2.6 \times 10^1$ | 2.41 | 3.32 |
| 25 | 300 | $1.2 \times 10^2$ | 2.08 | 3.65 |
| 0 | 300 | $1.1 \times 10^5$ | 5.04 | 0.69 |

It was noted that neither one of the treatments (ether amine or peracid) alone resulted in a significant reduction in spores. A concentration of 5000 ppm of ether amine achieved a log reduction of 0.27, and 300 ppm of peracid a log reduction of 1.02 (TABLE 3A) and 0.69 (TABLE 3C); 500 ppm of peracid achieved a log reduction of 3.15. It was further noted that application of part I and part II separately resulted in a synergistic effect, achieving significant log reductions. However, a high concentration (5000 ppm) of ether amine with 300 ppm of peracid resulted in a lower log reduction (2.23 in TABLE 3A and 1.62 in TABLE 3B), than lower concentrations. The synergistic effect was strongest at concentrations of less than 5000 ppm of ether amine.

Without wishing to be bound by theory, it was hypothesized that application of a high concentration (5000 ppm) of ether amine left residual ether amine on the fabric swatches, and when the swatches were moved into the second solution, the residual ether amine antagonistically reacted with the peracid.

Example 2

The treatment described above for Example 1 was applied to glass squares (5 mm×5 mm) in a first part of the experiment, where the first exposure time was 10 minutes (part I) and the second exposure time was 5 minutes (part II). In a second part of the experiment, the ether amine and peracid were mixed together prior to treatment, and the exposure time was 15 minutes. Results of the first part of the experiment are shown in TABLE 4A, and of the second part of the experiment in TABLE 4B.

TABLE 4A

Glass Surface, Consecutive Treatment

| Part I ether amine (ppm) | Part II peracid (ppm) | Average Survivors | Average Log | Log Reduction |
|---|---|---|---|---|
| 0 | 0 | $4.6 \times 10^6$ | 6.66 | — |
| 5000 | 300 | <10 | <1.00 | >5.66 |
| 0 | 300 | $2.0 \times 10^5$ | 5.30 | 1.36 |
| 5000 | 500 | <10 | <1.00 | >5.66 |
| 0 | 500 | $2.4 \times 10^3$ | 3.38 | 3.28 |

TABLE 4B

Glass Surface, Simultaneous Treatment

| Part I ether amine (ppm) | Part II peracid (ppm) | Average Survivors | Average Log | Log Reduction |
|---|---|---|---|---|
| 0 | 0 | $8.8 \times 10^5$ | 6.66 | — |
| 4500 | 300 | $2.6 \times 10^5$ | 5.41 | 0.53 |
| 4500 | 500 | $2.2 \times 10^5$ | 5.34 | 0.60 |

Consecutive treatment with part I and part II resulted in elimination of virtually all spores from the glass squares. In contrast, when ether amine and peracid were mixed together, little reduction of spores was achieved.

Without wishing to be bound by theory, it was hypothesized that that ether amine and peracid, when mixed together, act antagonistically against each other, thus preventing from acting against the spores.

Example 3

The treatment described in Example 2 was repeated at room temperature ("RT," approximately 23° C.). Part I was prepared with ether amine DA-1214 and Part II with peroxyacetic acid. The exposure times were 10 min for Part I and 5 min for Part II. The results are shown in Table 5 below.

TABLE 5

Glass surface, room temperature.

| Part I ether amine (ppm) | Part II peracid (ppm) | Average Survivors | Average Log | Log Reduction |
|---|---|---|---|---|
| 0 | 0 | $63 \times 10^5$ | 6.8 | — |
| 0 | 1000 | $>300 \times 10^3$ | >5.48 | <1.32 |
| 100 | 1000 | $77 \times 10^1$ | 2.89 | 3.91 |

It was observed that adding an ether amine treatment to the peracid improved the log reduction even at room temperature.

Example 4

Consecutive and simultaneous treatment with low concentration (100 ppm) of ether amine and peracetic acid was tested on fabric squares. The fabric squares were treated as in Example 1 with treatment times of 10 min (part I) and 5 minutes (part II), except with the simultaneous treatment, where ether amine and peracid were mixed prior to treatment and the exposure time was 5 minutes.

Results are shown in Table 6 below.

TABLE 6

Fabric swatches, Consecutive vs. Simultaneous Treatment

| | Part I ether amine (ppm) | Part II peracid (ppm) | Log Reduction |
|---|---|---|---|
| Consecutive | 0 | 0 | — |
| Consecutive | 0 | 300 | 0.85 |
| Consecutive | 100 | 300 | 3.45 |
| Simultaneous | 100 | 300 | 3.81 |

The log reductions of the consecutive and simultaneous treatments were very similar. It was concluded that as long as the concentration of ether amine is kept relatively low, the components (part I and part II) can be mixed together during treatment without significant loss of efficiency.

Example 5

Various ether amines were tested for their efficiency in eradicating bacterial spores from fabric swatches. The fabric swatches were treated according to ASTM protocol for evaluating laundry sanitizers and disinfectants (ASTM E2274-09). The ASTM protocol provides more realistic conditions for laundering textiles, where the tested textiles are imbedded within a bundle of fabrics to mimic the ability of the composition to penetrate the fabric with less exposure to the wash solution.

Three different ether amine solutions were tested: DA-1214 (octyl/decyloxypropyl-1,3-diaminopropane), DA-1618 (dodecyl/tetradecyloxypropyl-1,3-diaminopropane), and PA-14 (isodecyloxypropyl amine). Part I and Part II were both added together at the start of the experiment for a combined exposure time of 10 minutes. The solutions were made into deionized water as described in Example 1, with the pH adjusted to 9.0 by glycolic acid. However, PA-14 was already neutralized to pH 7 with sodium acetate. The log reduction of spores was measured in the wash solution and on the fabric swatch. The reduction of spores was compared to number of spores in the baseline treatment (water only). Results of the testing are shown in TABLE 7 below.

TABLE 7

Fabric Swatches (ASTM protocol), Simultaneous treatment

| Part I Ether Amine | Part I ether amine (ppm) | Part II peracid (ppm) | Wash Solution Log Reduction | Fabric Swatch Log Reduction |
|---|---|---|---|---|
| DA-1214 | 100 | 0 | 0.01 | 0.00 |
| DA-1618 | 100 | 0 | 0.12 | 0.02 |
| PA-14 | 100 | 0 | 0.17 | 0.07 |
| DA-1214 | 100 | 200 | 5.63* | 5.34 |
| DA-1618 | 100 | 200 | 5.63* | 5.97* |
| PA-14 | 100 | 200 | 5.63* | 4.63 |
| — | 0 | 200 | 5.33 | 2.65 |

*Killed all spores present

It was found that the amines alone had virtually no impact of spores in either the wash solution or on the fabric swatch, while the peracid alone was effective in eliminating spores in the wash solution, but less so on the fabric swatch. Consecutive treatments with each of the ether amines and peracid eliminated all of the spores in the wash solution and were also effective against spores on the fabric swatches. It was found that of the ether amines tested, DA-1618 was the most effective against spores on fabric swatches.

Example 6

Treatment of fabric swatches was tested in pH-adjusted hard water. The wash solution contained 500 ppm synthetic hard water, and the pH was adjusted to 10.5 with NaOH prior to peracid addition. After the addition of the peracid, pH of the wash solution was between 7-8. DA-1214 was used as the ether amine and peracetic acid as the peracid.

The log reduction of spores was measured in the wash solution and on the fabric swatch. The reduction of spores was compared to number of spores in the baseline treatment (water only). The combined treatment time was 10 minutes. Results of the testing are shown in TABLE 8 below.

TABLE 8

Fabric Swatches (ASTM E2274), Simultaneous Treatment, Hard Water

| Part I ether amine (ppm) | Part II peracid (ppm) | Wash Solution Log Reduction | Fabric Swatch Log Reduction |
|---|---|---|---|
| 0 | 200 | 5.30 | 3.01 |
| 100 | 200 | 6.15* | 6.30* |

*Killed all spores present

It was found that the treatment with ether amine and peracid killed all of the spores present in the wash solution and on the fabric swatch. It was concluded that the effectiveness of the consecutive treatment with ether amine and peracid was not reduced by the alkaline hard water.

Example 7

The use of different peracids was tested. Fabric swatches were treated using the ASTM test described in Example 5. Part I was prepared with 100 ppm ether amine (DA-1618). Part II was prepared with 200 ppm of peroxyacetic acid ("POAA") or peroxyoctanoic acid ("POOA"). When both Part I and Part II were used, the chemicals were added simultaneously. The exposure time was 10 min at 50° C. The results are shown in TABLE 9 below.

TABLE 9

Peracid comparison.

| Part I Ether amine 100 ppm | Part II Peracid 200 ppm | Wash Solution Log Reduction | Carrier log reduction |
|---|---|---|---|
| — | POAA | 4.40 | 1.78 |
| DA-1618 | POAA | 6.00* | 5.78* |
| — | POOA | 6.00* | 5.35 |
| DA-1618 | POOA | 6.00* | 1.70 |

It was observed that adding ether amine to peroxyacetic acid resulted in a significant increase in the kill. Peroxyoctanoic acid alone was nearly as effective as peroxyacetic acid and ether amine together. However, adding ether amine to the peroxyoctanoic acid reduced the kill. It was noted that peroxyoctanoic acid and ether amine are both very hydrophobic, and thus have an affinity to each other. It was therefore hypothesized that when the two chemicals were added simultaneously in solution they agglomerated together and caused a reduction in the kill.

While certain embodiments of the invention have been described, other embodiments may exist. While the specification includes a detailed description, the invention's scope is indicated by the following claims. Furthermore, while the specification has been described in language specific to structural features and/or methodological acts, the claims are not limited to the features or acts described above. Rather, the specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A method for eliminating bacterial spores on an article suspected of contamination with bacterial spores, the method comprising:
    preparing a first use solution by mixing about 10 to about 2,000 ppm of ether amine in water and a second use solution by mixing about 10 to about 2,000 ppm of percarboxylic acid in water;
    applying the first use solution to the article; and
    applying the second use solution to the article.

2. The method of claim 1, wherein the ether amine comprises one or more ether amines having 1-22 carbon atoms.

3. The method of claim 1, wherein the ether amine comprises one or more ether amines having 10-18 carbon atoms.

4. The method of claim 1, wherein the first use solution comprises 25-1,500 ppm ether amine.

5. The method of claim 1, wherein the first use solution comprises 25-1,000 ppm ether amine.

6. The method of claim 1, wherein the first use solution comprises 50-500 ppm ether amine.

7. The method of claim 1, wherein the percarboxylic acid comprises one or more percarboxylic acids having 2-12 carbon atoms.

8. The method of claim 1, wherein the second use solution comprises 10-1,500 ppm percarboxylic acid.

9. The method of claim 1, wherein the second use solution comprises 50-1,000 ppm percarboxylic acid.

10. The method of claim 1, wherein the second use solution comprises 50-500 ppm percarboxylic acid.

11. The method of claim 1, wherein the method is capable of at least 2-log reduction of bacterial spores selected from C. diff, C. botulinum, C. sporogenes, B. cereus, and B. subtilis.

12. The method of claim 1, wherein the method is capable of at least 3-log reduction of bacterial spores selected from C. diff, C. botulinum, C. sporogenes, B. cereus, and B. subtilis.

13. The method of claim 1, wherein the method is capable of at least 4-log reduction of bacterial spores selected from C. diff, C. botulinum, C. sporogenes, B. cereus, and B. subtilis.

14. The method of claim 1, wherein the article comprises a textile or a hard surface.

15. The method of claim 1, wherein at least one of the first use solution and second use solution further comprises one or more surfactants.

16. The method of claim 1, wherein at least one of the first use solution and the second use solution further comprises one or more pH modifiers.

17. The method of claim 1, wherein the first use solution and the second use solution are applied simultaneously to the article.

18. The method of claim 1, wherein the first use solution and the second use solution are applied consecutively to the article.

19. The method of claim 1, wherein the first use solution and the second use solution are applied cumulatively to the article.

20. The method of claim 1, wherein one of the first use solution and the second use solution is a laundry booster.

21. The method of claim 1, wherein one of the first use solution and the second use solution is applied to a hard surface of the article.

22. The method of claim 21, wherein one of the first use solution and the second use solution is applied to the article by spraying, pouring, wiping, or mopping.

23. A method for eliminating bacterial spores, the method comprising:
   preparing a first use solution by mixing about 10 to about 3,000 ppm of ether amine in water;
   preparing a second use solution by mixing about 10 to about 3,000 ppm of percarboxylic acid in water;
   applying the first use solution to an article suspected of contamination with bacterial spores;
   applying the second use solution the article suspected of contamination with bacterial spores.

24. The method of claim 23, wherein the first use solution comprises 25-2,000 ppm ether amine.

25. The method of claim 23, wherein the first use solution comprises 50-1,500 ppm ether amine.

26. The method of claim 23, wherein the first use solution comprises 50-1,000 ppm ether amine.

27. The method of claim 23, wherein the second use solution comprises 10-2,000 ppm percarboxylic acid.

28. The method of claim 23, wherein the second use solution comprises 50-1,500 ppm percarboxylic acid.

29. The method of claim 23, wherein the second use solution comprises 50-1,000 ppm percarboxylic acid.

30. The method of claim 23, wherein applying the first use solution comprises immersing the article in the first use solution, and applying the second use solution comprises immersing the article in the second use solution, the method further comprising draining the first use solution before applying the second use solution.

31. The method of claim 23, wherein the first use solution and the second use solution are applied simultaneously to the article.

32. The method of claim 23, wherein the first use solution and the second use solution are applied cumulatively to the article.

* * * * *